(12) United States Patent
Obratil et al.

(10) Patent No.: US 10,508,967 B2
(45) Date of Patent: Dec. 17, 2019

(54) LEAK ISOLATION SYSTEM

(71) Applicant: American Sterilizer Company, Mentor, OH (US)

(72) Inventors: Jeffrey Obratil, Sugar Hill, GA (US); Joseph William Clemens, Plainwell, MI (US); David James Glaspell, Wattsburg, PA (US)

(73) Assignee: American Sterilizer Company, Mentor, OH (US)

( * ) Notice: Subject to any disclaimer, the term of this patent is extended or adjusted under 35 U.S.C. 154(b) by 113 days.

(21) Appl. No.: 15/848,573

(22) Filed: Dec. 20, 2017

(65) Prior Publication Data

US 2018/0283979 A1    Oct. 4, 2018

Related U.S. Application Data

(60) Provisional application No. 62/478,200, filed on Mar. 29, 2017.

(51) Int. Cl.
*G01M 3/28* (2006.01)

(52) U.S. Cl.
CPC ................ *G01M 3/2815* (2013.01)

(58) Field of Classification Search
None
See application file for complete search history.

(56) References Cited

U.S. PATENT DOCUMENTS

| 1,936,552 | A | * | 11/1933 | Goss | F16L 19/0218 |
| | | | | | 285/341 |
| 3,577,769 | A | * | 5/1971 | Roberts | G01M 3/229 |
| | | | | | 73/40.7 |
| 3,822,585 | A | * | 7/1974 | Toback | G01M 3/26 |
| | | | | | 73/49.2 |
| 5,837,193 | A | | 11/1998 | Childers et al. | |
| 6,435,010 | B1 | | 8/2002 | Johnson et al. | |
| 6,485,684 | B1 | | 11/2002 | Mapson et al. | |
| 6,629,043 | B1 | * | 9/2003 | Poteat | G01M 3/202 |
| | | | | | 702/51 |
| 2011/0174060 | A1 | | 7/2011 | Guazzo et al. | |
| 2017/0197003 | A1 | * | 7/2017 | Taggart | A61L 2/202 |

FOREIGN PATENT DOCUMENTS

| AU | 200323426 B1 | 3/2004 |
| CN | 201724796 U | 1/2011 |

OTHER PUBLICATIONS

Agilent Technologies, "Agilent Leak Detection." PDF catalog, www.agilent.comi/cs/library/catalogs/public/09_Leak_Detectors.pdf._22_Aug._2015.

* cited by examiner

*Primary Examiner* — Paul M. West
*Assistant Examiner* — Mark A Shabman
(74) *Attorney, Agent, or Firm* — Kusner & Jaffe

(57) ABSTRACT

A leak detection system for use in a vacuum sterilization chamber having a plurality of piping sections that are connected to the sterilization chamber through openings along an inner surface of the sterilization chamber.

11 Claims, 5 Drawing Sheets

LEAK ISOLATION SYSTEM

RELATED APPLICATIONS

This application claims the benefit of U.S. Provisional Application No. 62/478,200, filed Mar. 29, 2017, which is hereby fully incorporated herein by reference.

FIELD OF THE INVENTION

The present invention relates to vacuum sterilizers, and more particularly, to a system for isolating and locating leaks in sections of a vacuum sterilizer.

BACKGROUND OF THE INVENTION

Vacuum sterilizers operate by drawing a vacuum within a chamber and exposing articles within the chamber to steam or a vaporized sterilant. Important in the operation of such sterilizers is maintaining the vacuum within the chamber at desired levels. Most vacuum sterilizers have diagnostic systems that have a leak detection cycle to detect leaks within the system. A problem with existing diagnostic systems is that, although they can detect a vacuum leak within the sterilizer, the diagnostic routine cannot isolate regions or sections of the sterilizer where the leak may exist.

Presently, when a leak is detected, service personnel typically replace parts in certain areas or sections of the sterilizer and rerun the leak detection cycle to determine if the replaced parts corrected the problem. As will be appreciated, such a procedure is very time consuming and not efficient in that a typical leak detection cycle can take approximately forty to forty-five minutes to run. In this respect, the leak detection cycle utilizes a vacuum source (pump or ejector) within a sterilizer to draw a vacuum on the entire system, including the sterilization chamber which comprises the largest volume of the overall system. Moreover, most leak detection cycles are performed under normal operating conditions, namely, by heating the sterilization chamber, which heating is part of a typical sterilization cycle. The heating typically involves bringing the sterilization chamber to a temperature of about 250 degrees Fahrenheit (120 C). Once heated, the sterilization chamber must be allowed to cool before service personnel can work on the system as to avoid personal injury and/or damage to parts of the sterilizer during disconnection while such parts are hot. Thus, the present trial-and-error replacement of parts and repeated running of leak detection cycles to detect a leak can be long, time-consuming and inefficient.

Accordingly, there is a need for a system that allows service personnel to isolate sections of a vacuum sterilizer to quickly detect which section of the sterilizer is leaking.

The present invention provides a leak locating system for isolating sections of piping within a vacuum sterilizer, which detection system can connect such sections to a vacuum source of the steam sterilizer and then detect leaks in the isolated sections.

SUMMARY OF THE INVENTION

In accordance with the present invention, there is provided a leak detection system for use in a vacuum sterilization chamber having a plurality of piping sections that are connected to the sterilization chamber through openings along an inner surface of the sterilization chamber. The leak detection system is comprised of an elongated flexible tubing dimensioned to connect to openings in the sterilization chamber. A connector is connected to each end of the tubing. The connector is dimensioned to sealingly engage against an opening in the sterilization chamber and to communicate a passage through the tubing with a piping section connected to the sterilization chamber. A sensing device is attached to the tubing and is operable to measure changes in pressure. Valves disposed within the tubing are operable to isolate one opening in the steam sterilizer from another. The valves are disposed relative to the sensing device to allow for selective isolation and sensing of pressure changes in one of the piping sections.

An advantage of the present invention is a leak detection system for isolating and testing sections of a vacuum sterilizer.

Another advantage of the present invention is a leak detection system, as described above, that allows individual testing of isolated sections of a vacuum sterilizer.

Another advantage of the present invention is a leak detection system that enables a technician to test a vacuum sterilizer in less time than running a leak detection cycle of the sterilizer.

Another advantage of the present invention is a leak detection system that allows a technician to search for leaks in a sterilizer while the sterilizer is in a cooled state, thereby making it safer to work around sterilizer piping and sterilizer chamber.

A still further advantage of the present invention is a leak detection system for a vacuum sterilizer that reduces troubleshooting time by allowing the technician to isolate sections of piping of the sterilizer and determine if a leak exists in a tested section.

A still further advantage of the present invention is a leak detection system that is attachable and operable with most existing vacuum sterilizers.

A still further advantage of the present invention is a leak detection system that is relatively lightweight and portable and can be transported by a technician to a worksite.

A still further advantage of the present invention is a leak detection system that allows a technician to more quickly isolate and correct leaks in a vacuum sterilizer.

DETAILED DESCRIPTION OF THE PREFERRED EMBODIMENTS

Figure 1:
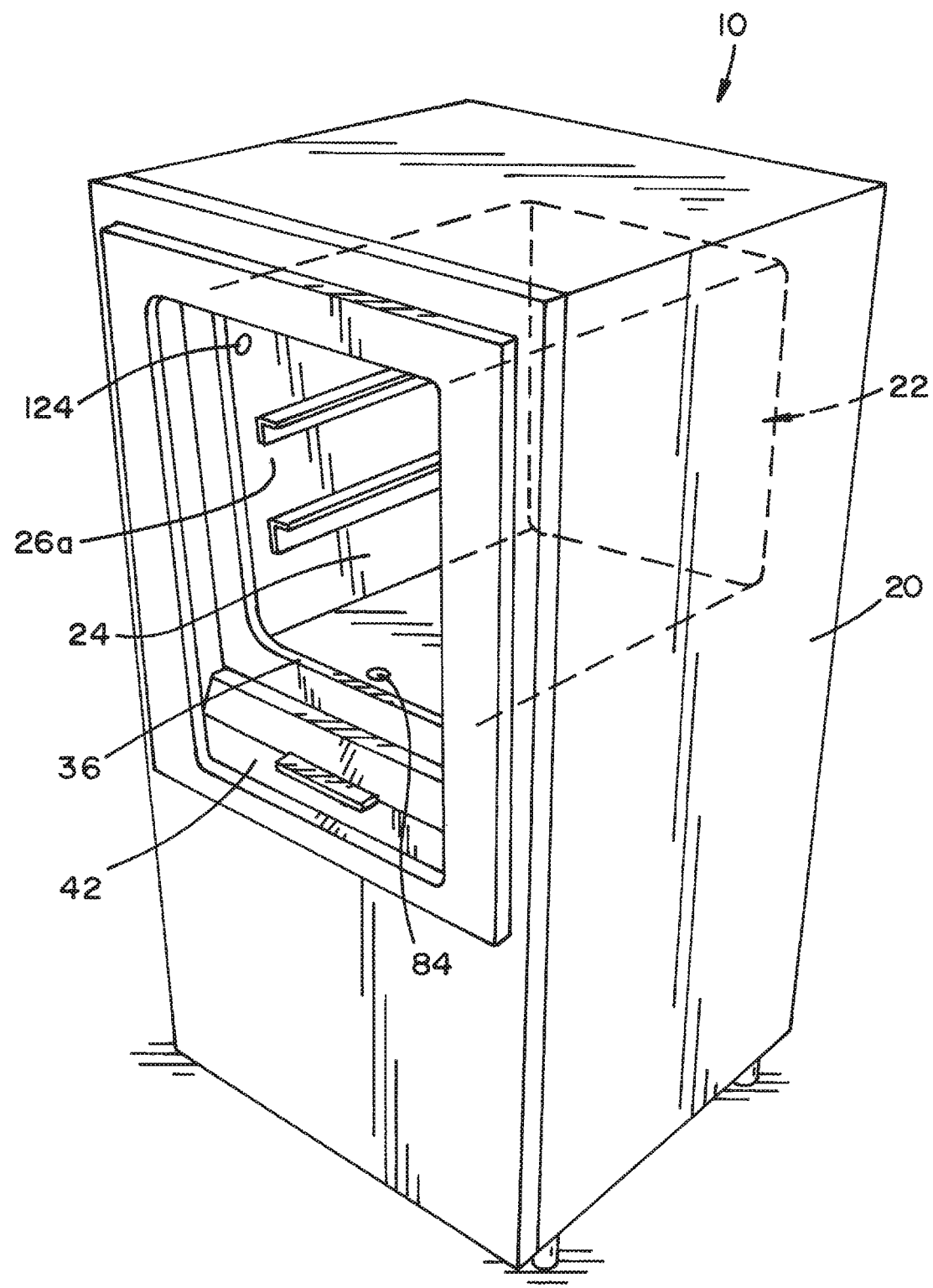
FIG. 1 is a perspective view of a conventional vacuum sterilizer.
Figure 2:
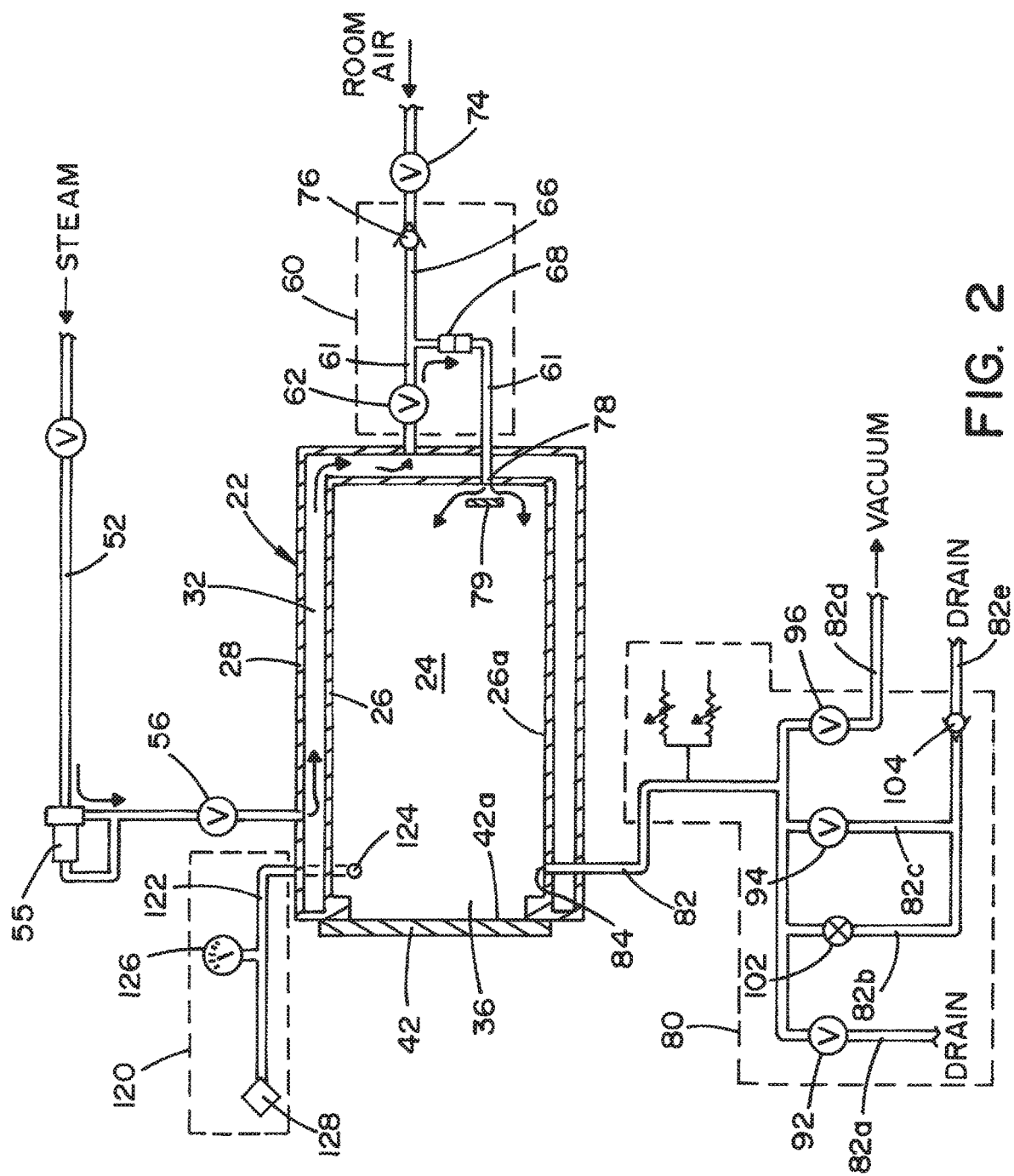
FIG. 2 is a schematic diagram of portions of the vacuum sterilizer shown in FIG. 1 illustrating portions of different piping sections that form part of the sterilizer and that communicate with a vacuum source.

Referring now to the drawings wherein the showings are for the purposes of illustrating an embodiment of the invention only and not for the purposes of limiting same, FIG. 1 is a perspective view of a conventional vacuum sterilizer. Sterilizer 10 is basically comprised of an outer housing 20 enclosing a body 22 that defines an internal sterilization chamber 24. In the embodiment shown, sterilizer body 22 is generally tubular in shape. Sterilizer body 22 is comprised of an inner wall 26 and an outer wall 28, as schematically illustrated in FIG. 2. Outer wall 28 is spaced from inner wall 26 to define a cavity 32 surrounding sterilization chamber 24. Cavity 32 is to be used as a steam jacket, as shall be described in greater detail below. One end of the sterilizer body 22 is closed and the other end of sterilizer body 22 defines an opening 36. A movable door 42 traverses opening 36 to open and close access to sterilization chamber 24. An inner surface 26a of inner wall 26 and inner surface 42a of door 42 basically define sterilization chamber 24.

Referring now to FIG. 2, a simplified piping diagram showing sections of piping that connect to sterilization chamber 24 is shown. As will be appreciated by those skilled in the art, FIG. 2 illustrates only portions of a conventional steam sterilizer. Specifically, FIG. 2 illustrates those sections of piping that are connected to sterilizer chamber 24 and that are typically under vacuum during a sterilization cycle. In this respect, sterilizer 10 and the piping sections hereinafter described, in and of themselves, form no part of the present invention and are described for the purpose of illustrating the application of use of a leak isolation system that shall be described in greater detail below.

As illustrated in FIG. 2, a steam inlet line 52 connects a steam source to cavity 32 of body 22. A regulator 55 and a control valve 56 are disposed in steam inlet line 52 to control flow therethrough. In addition to steam inlet line 52, FIG. 2 illustrates three piping sections that connect to sterilization chamber 24 and that are typically under vacuum during a vacuum sterilization cycle. In this respect, FIG. 2 illustrates a steam piping section 60, a drain piping section 80, and a transducer piping section 120.

Steam Piping Section 60

Steam piping section 60 is comprised of a connecting line 61 that connects cavity 32 of the sterilizer body 22 to internal sterilization chamber 24. A valve 62 is disposed in connecting line 61 to limit flow through connecting line 61 to steam flowing from cavity 32 to sterilization chamber 24. In the embodiment shown, a pipe union 68 is disposed in connecting line 61.

A vent line 66 is connected to steam connecting line 61. Vent line 66 connects to an external air source, as schematically illustrated in FIG. 2. A filter (not shown) is typically provided in vent line 66 to filter air flowing through vent line 66. A valve 74 controls flow through vent line 66. A check valve 76 is also provided in vent line 66, between valve 74 and sterilization chamber 24, to limit air flow through vent line 66 to air flowing into sterilization chamber 24. Where connecting line 61 connects to sterilization chamber 24, an opening 78 is defined in inner surface 26a of inner wall 26. A baffle 79 is shown opposite opening 78 to control the flow of steam and air into sterilization chamber 24 during operation of sterilizer 10.

Drain Piping Section 80

Drain piping section 80 is basically comprised of a drain line 82 extending from sterilization chamber 24. Drain line 82 defines an opening 84 in inner surface 26a of inner wall 26. In a typical sterilizer, drain line 82 branches off into several branch lines to different portions of sterilizer 10. In the embodiment shown, four branch drain lines, designated 82a, 82b, 82c and 82d, branch off from drain line 82. Control valves 92, 94, 96 control the flow through branch lines 82a, 82b, 82d. A steam trap 102 is disposed in branch line 82b. In the embodiment shown, branch lines 82b and 82c are joined to form branch line 82e. A directional check valve 104 is provided in branch line 82e downstream of branch lines 82b, 82c. Branch line 82d communicates with a vacuum source, as shown in FIG. 2. In a typical steam system 10, a vacuum pump or vacuum ejector is used to create a vacuum in sterilization chamber 24.

Transducer Piping Section 120

Transducer piping section 120 is basically comprised of a pipe 122 extending from the sterilization chamber 24. Pipe 122 defines an opening 124 in inner surface 26a of inner wall 26. In the embodiment shown, a pressure gauge 126 is attached to transducer pipe 122 to provide a visual indication of pressure within sterilization chamber 24. A pressure transducer 128 is attached to transducer pipe 122 to provide an electrical signal indicative of a pressure within sterilization chamber 24.

Each piping sections 60, 80, 120 as heretofore described communicates with sterilization chamber 24 and are exposed to a vacuum during a sterilization cycle. As such, piping sections 60, 80, 120 represent areas of sterilizer 10 were leaks may occur. Specifically, it is at locations where valves, gauges and pipe fitting connect that leaks can occur.

Leak Detection System 200

Figure 3:
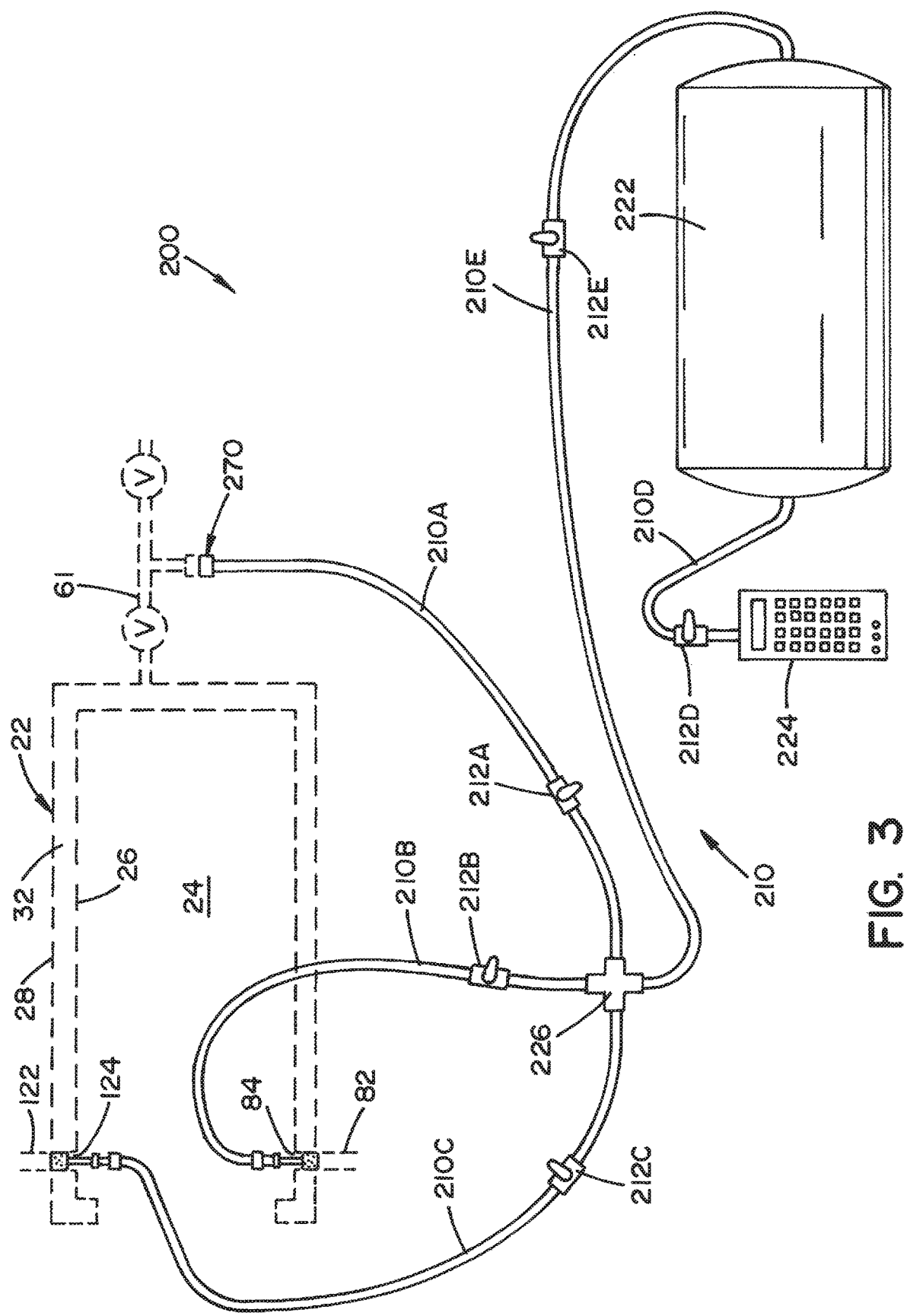
FIG. 3 is a schematic of a leak detection system for isolating sections of a vacuum sterilizer and for testing such sections for leaks.

Referring now to FIG. 3, leak detection system 200 isolates sections of a vacuum sterilizer to respectively determine whether leaks occur in the isolated sections. Leak detection system 200 is comprised of elongated, flexible tubing 210 dimensioned to connect to openings 78, 84, 124 in the sterilization chamber 24. In the embodiment shown, five tubing sections 210A, 210B, 210C, 210D, 210E extend from and connect to accumulator tank 222 and to meter 224. More specifically, accumulator tank 222 is connected to meter 224 by tubing section 210D. Tubing section 210E connects to tank 222 to a manifold 226, which in turn connects tubing sections 210E to tubing sections 210A, 210B, 210C. Manual control valves, designated 212A, 212B, 212C, 212D and 212E, are provided in tubing sections 210A, 210B, 210C, 210D and 210E respectively, as shown in FIG. 3, to control flow through the respective tubing sections. The ends of tubing sections 210A, 210B, 210C include connectors to connect to the openings 78, 84, 124 in sterilization chamber 24 or to connect to piping extending from sterilization chamber 24.

Figure 5:
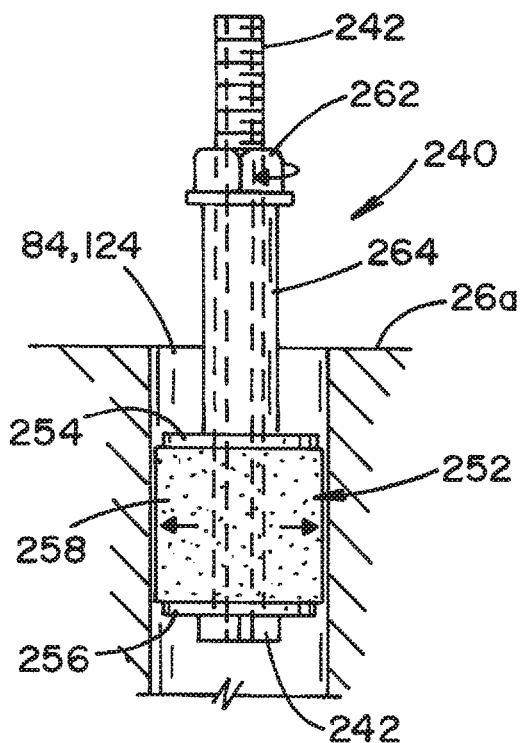
FIG. 5 is a sectional view of an inner surface connector for attachment to an opening to a piping section within the sterilizer, showing the connector in a non-sealing configuration.
Figure 6:
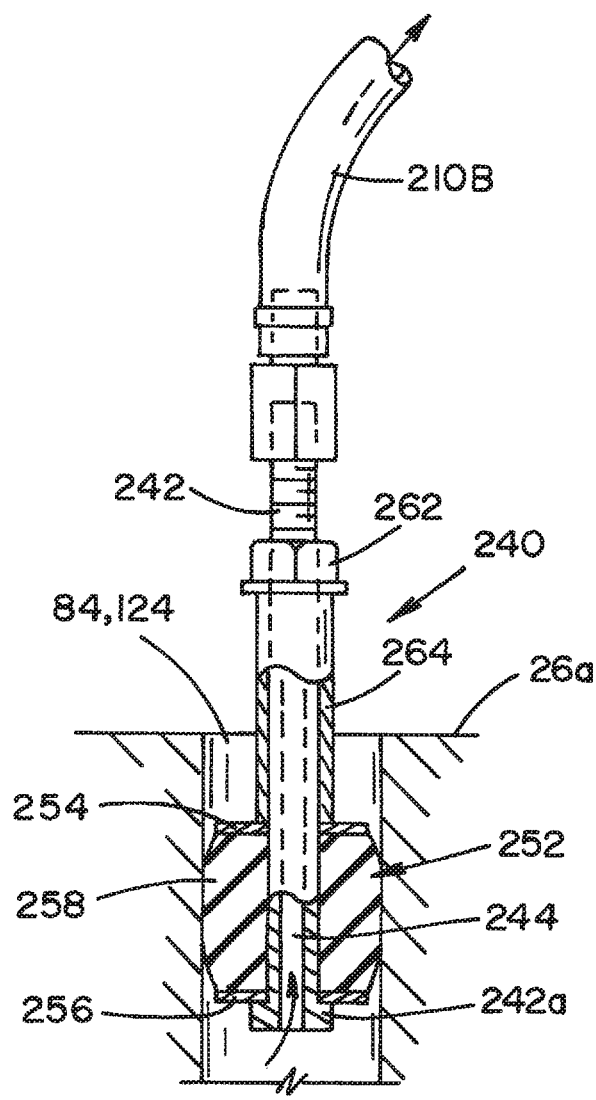
FIG. 6 is a sectional view of the inner surface connector shown in FIG. 5, showing the connector in a sealing configuration with the opening in a sterilization chamber.

Referring now to FIGS. 5 and 6, an inner surface connector 240 is best seen. Inner surface connector 240 is provided to connect tubing 210 to openings 84, 124 within sterilization chamber 24. Inner surface connector 240 is basically comprised of an elongated tubular shaft 242 having a flange 242a at one end thereof. An elongated passageway 244 extends axially through shaft 242. Inner surface connector 240 includes an expansion assembly 252 surrounding a portion of the shaft. In the embodiment shown, the expansion member is comprised of spaced apart annular plates 254, 256 mounted to tubular shaft 242. A resilient flexible expansion member 252 is disposed between the plates 254, 256. Plate 256 abuts flange 242 and is fixed relative thereto. Plate 254 is releasable moveable toward plate 256, such that resilient expansion member 258 is compressed between plates 254, 256. In the embodiment shown, tubular shaft 242 is threaded and a matchingly threaded fastener 262 is screwed onto shaft 242 to tighten or release plate 254 against expansion member 258. A tubular sleeve 264 is disposed around shaft 242 between fastener 267 and plate 254. In this respect, expansion member 258 is dimensioned to be inserted into opening 84 or 124 in sterilization chamber 24 and when compressed between plates 254, 256 to expand into sealing surface engagement with the inner surface of the pipe or tube that defines opening 84 or 124. When in sealing engagement with opening 84 or 124 in sterilization 24, passageway 244 through tubular shaft 242 communicates with passageway defined by the pipe forming opening 84 or 124.

In accordance with another aspect of the present invention, an external surface connector 270 may be provided to connect to an external surface of a pipe or tubing that defines or connects with an opening within sterilization chamber 24. In this respect, some openings within sterilization chamber 24 may be obstructed by components within sterilization chamber 24, such as baffle 79, that obstruction prevents an inner surface connector 240, as described above, from being easily inserted and attached therein. Alternately, it may be simpler to access piping externally of the sterilization chamber. In the embodiment shown, external surface connector 270 is basically a conventional pipe fitting or part of a pipe union that could connect a tubing section to a pipe that defines an opening with sterilization chamber 24.

Figure 4:
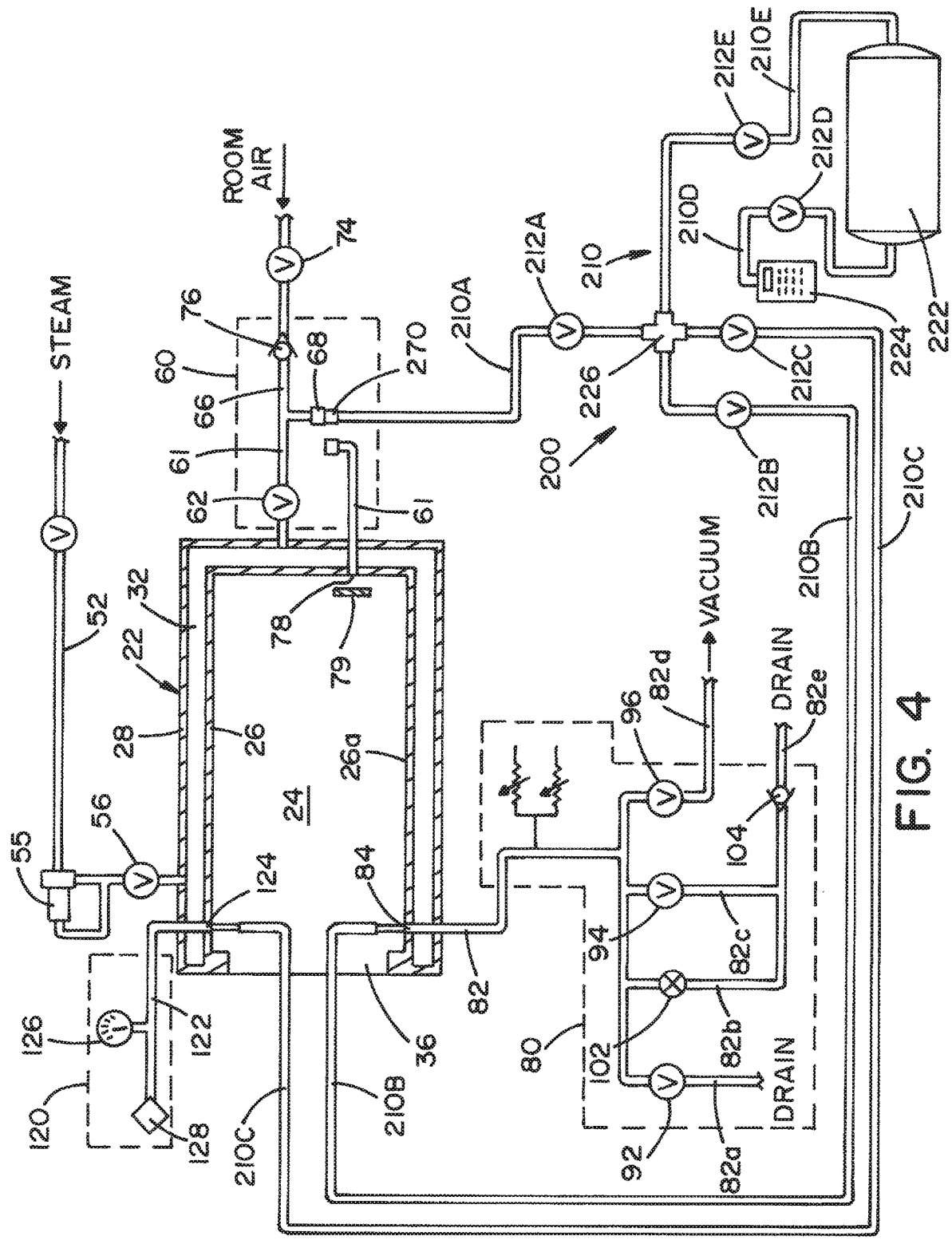
FIG. 4 is a schematic diagram showing the leak detection system of FIG. 3 connected to an opening within the sterilization chamber.

Referring now the operation and use of leak detection system 200, if the leak detection cycle of sterilizer 10 indicates a leak in the system, a service technician would connect leak detection system 200 to sterilizer 10, as schematically illustrated in FIG. 4. Specifically, openings 78, 84, 124 within sterilization chamber 24, as illustrated in FIG. 4. Specifically, for openings 84, 124 that are easily accessible from inside sterilization chamber 24, inner surface connectors 240 are sealed against the inner surface of openings 84, 124 by compressing the expansion member 258 on connectors 240 by tightening threaded fasteners 262 onto tubular shaft 242. For openings that are obstructed, or that are easier to access outside of sterilization chamber 24 (such as opening 78 in the drawings that is obstructed by baffle 79), external surface connector 270 can be used to connect to a section of pipe that defines opening 78. For example, union 68 in steam inlet line 61 can be disconnected and external surface connector 270 on tubing section 210A can be connected to the mating part of union 68. In this respect, removal of baffle 79 is time consuming and complicated. Thus, it is easier in this situation to connect tubing 210 to a portion of the piping outside sterilization chamber 24.

As best seen in FIG. 4, when the leak detection system is connected to a sterilizer, as described above, aforementioned piping sections 60, 80, 120 are connected to each other by tubing 210. As will be appreciated, such connections isolate piping sections 60, 80, 120 from sterilization chamber 24. According to one aspect of the present invention, the vacuum source within sterilizer 10, specifically attached to drain piping section 80 of sterilizer 10, is connected to steam piping section 60 and to piping transducer section 120 by tubing 210.

With leak detection system 200 connected as described above, a service technician moves valves 212A, 212B, 212C, 212D, and 212E in tubing sections 210A, 210B, 210C, 210D, 210E to an open position. With all of piping sections 60, 80, 120 communicating with each other by means of tubing 210, the service technician activates vacuum 106 (vacuum pump) of sterilizer 10 to draw vacuum on all of piping sections 60, 80, 120 and on accumulator tank 222. Meter 224 senses the vacuum level on piping sections 60, 80, 120 and tubing 210. Once a desired vacuum level has been established, valves 212A, 212C to steam piping section 60 and transducer piping section 120 are closed to isolate these sections from drain piping section 80. The meter then monitors the pressure level of drain piping section 80 over time to determine whether the vacuum on drain piping section 80 is decaying. If no leak in vacuum pressure is detected, valve 212B in tubing section 210A is closed off to isolate drain piping section 80 from meter 224. Valve 212A to steam piping section 60 is then opened to communicate steam piping section 60 with meter 224. Meter 224 should read the same vacuum level on steam piping section 60 if no leak has occurred. In this respect, a difference in pressure between pressure detected within the steam piping section 60 and that previously monitored on drain piping section 80 is an indication of a leak in the steam piping section 60. If no noticeable change has occurred between the pressure (vacuum) in drain piping section 80 and steam piping section 60, the service technician can monitor steam piping section 60 over a predetermined period of time to confirm the initial detected pressure level of steam piping section 60 is holding. If no leak is detected, valve 212A in tubing section 210 to steam piping section 60 is closed to isolate steam piping section 60 from meter 224.

Then, valve 212C in tubing section 210C to transducer piping section 120 is opened to connect transducer piping section 120 to meter 224. The foregoing process is then repeated to detect if the vacuum level within transducer piping section 120 has decayed during the testing of drain piping section 80 and steam piping section 60, or whether the vacuum level is decaying while meter 224 is exposed to transducer piping section 120.

The present invention thus provides a leak detection system 200 that can isolate and test selective sections of a sterilizer. Moreover, use of leak detection system 200 does not require drawing a vacuum on sterilization chamber 24 and further does not require heating sterilization chamber 24 to conduct the leak detection analysis. Using leak detection system 200 described above, a service technician can more quickly isolate sections of a sterilizer to determine if a leak exists in one of the sections, thereby focusing further repair efforts to a specific area of the sterilizer. Leak detection system 200 is relatively lightweight and portable and is adaptable to many types of existing vacuum sterilizer systems. Still further, leak detection system 200, as described above, utilizes the vacuum pump of the sterilizer to generate the vacuum necessary to test the respective piping sections of the system.

The present invention has been described with respect to a preferred embodiment. As will be appreciated by those skilled in the art, other types of connectors could be used to connect and seal to openings within the sterilization chamber or to piping fittings extending through the sterilization chamber.

Having described the invention, the following is claimed:

1. A leak detection system for use in a vacuum sterilization chamber, the vacuum sterilization chamber having an inner surface in which one or more openings are defined such that one or more piping sections are respectively connected to the vacuum sterilization chamber through the openings, the leak detection system comprising:
   an elongated flexible tubing having one or more ends respectively dimensioned to connect to the openings;
   one or more connectors respectively connected to the ends, the connectors being respectively dimensioned to sealingly engage the openings and to respectively communicate passages through the elongated flexible tubing with the piping sections, one or more of the connectors being inner surface connectors respectively comprising expansion members, the expansion members being respectively dimensioned to expand into sealing engagement with the openings and surface engagement with the inner surface defining the openings;

a sensing device attached to the elongated flexible tubing operable to measure changes in pressure in the piping sections; and valves disposed relative to the sensing device and within the elongated flexible tubing, the valves being operable to selectively isolate one or more of the openings from others of the openings to enable the sensing device to measure the pressure changes in one or more of the piping sections respectively corresponding with the isolated openings.

2. A leak detection system as described in claim 1, wherein one of the piping sections includes a vacuum source.

3. A leak detection system as described in claim 2, wherein said vacuum source is a vacuum pump.

4. A leak detection system as described in claim 1, wherein said inner surface connectors further respectively comprise inner passageways extending through said expansion members.

5. A leak detection system as described in claim 1, wherein one of said connectors is an external surface connector comprising a pipe fitting dimensioned to attach to a pipe extending through said inner surface, said pipe defining one of said openings.

6. A leak detection system as described in claim 1, wherein said elongated flexible tubing includes three tubing sections, each of the tubing sections having one of the ends of the elongated flexible tubing, two of said tubing sections respectively comprising the inner surface connectors, one of said tubing sections including an external surface connector, the external surface connector comprising a pipe fitting dimensioned to attach to a pipe extending through said inner surface, said pipe defining one of said openings.

7. A leak detection system as described in claim 6, wherein said inner surface connectors further respectively comprise inner passageways extending through said expansion members.

8. A leak detection system as described in claim 1, further comprising an accumulator tank of a predetermined volume connected to said elongated flexible tubing.

9. A leak detection system as described in claim 1, wherein the ends of the elongated flexible tubing respectively include the connectors.

10. A leak detection system as described in claim 1, wherein said elongated flexible tubing comprises one or more tubing sections connected to each other at a manifold, each of the tubing sections having one of the ends of the elongated flexible tubing, and wherein the valves within the elongated flexible tubing are respectively disposed between the ends of the tubing sections and the manifold.

11. A leak detection system for use in a chamber, the chamber having an inner surface in which one or more openings are defined such that one or more piping sections are respectively connected to the chamber through the openings, the leak detection system comprising:

an elongated flexible tubing having one or more ends dimensioned to connect to the openings;

one or more connectors respectively connected to the ends, the connectors being respectively dimensioned to sealingly engage the openings and to respectively communicate passages through the elongated flexible tubing with the piping sections, one or more of the connectors being inner surface connectors respectively comprising expansion members, the expansion members being respectively dimensioned to expand into sealing engagement with the openings and surface engagement with the inner surface defining the openings;

a sensing device attached to the elongated flexible tubing operable to measure changes in pressure in the piping sections; and valves disposed relative to the sensing device and within the elongated flexible tubing, the valves being operable to selectively isolate one or more of the openings from others of the openings to enable the sensing device to measure the pressure changes in one or more of the piping sections respectively corresponding with the isolated openings.

* * * * *